(12) United States Patent
Cimpoia et al.

(10) Patent No.: US 7,955,835 B2
(45) Date of Patent: Jun. 7, 2011

(54) STEREOSELECTIVE PROCESS FOR THE PRODUCTION OF DIOXOLANE NUCLEOSIDE ANALOGUES

(75) Inventors: Alex Cimpoia, Verdun (CA); James Joseph LaLonde, Palo Alto, CA (US)

(73) Assignee: SHIRE Canada Inc., Laval, Quebec (CA)

( * ) Notice: Subject to any disclaimer, the term of this patent is extended or adjusted under 35 U.S.C. 154(b) by 573 days.

(21) Appl. No.: 10/535,235

(22) PCT Filed: Nov. 18, 2003

(86) PCT No.: PCT/CA03/01798
§ 371 (c)(1),
(2), (4) Date: Dec. 19, 2005

(87) PCT Pub. No.: WO2004/048590
PCT Pub. Date: Jun. 10, 2004

(65) Prior Publication Data
US 2006/0134763 A1    Jun. 22, 2006

Related U.S. Application Data

(60) Provisional application No. 60/426,821, filed on Nov. 18, 2002.

(51) Int. Cl.
*C12P 41/00* (2006.01)
(52) U.S. Cl. .......... 435/280; 435/118; 435/135; 435/88; 435/19; 514/44
(58) Field of Classification Search .................. None
See application file for complete search history.

(56) References Cited

U.S. PATENT DOCUMENTS
2001/0049372 A1    12/2001    Nguyen-Ba

FOREIGN PATENT DOCUMENTS
| WO | WO 0039143 | | 7/2000 |
| WO | WO 00/47759 | * | 8/2000 |
| WO | WO 0047759 | | 8/2000 |

OTHER PUBLICATIONS

Ferrero et al., Monatshefte für Chemie, 2000, vol. 131, p. 585-616.*
Adler et al., JBC, 1961, vol. 236, No. 12, p. 3240-3245.*
Martinelle et al., Biochimica et Biophysica Acta, 1995, vol. 1258 p. 272-276.*

Janes et al: "Protease -Mediated Separation of Cis and Trans Diastereomers of 2(R,S)- benzyloxymethyl-4(S)-carboxylic Acid 1,3-Dioxolane Methy Ester: Intermediates for the Synthesis of Dioxolane Nucleosides" Journal of Organic Chemistry, American Chemical Society, Easton, US, vol. 64, Nov. 19, 1999, pp. 9019-9029, XP002137411.

\* cited by examiner

*Primary Examiner* — Kade Ariani
(74) *Attorney, Agent, or Firm* — Millen, White, Zelano & Branigan, P.C.

(57) ABSTRACT

The present invention relates to a process for producing compounds of formula (I) and (VII); said process comprising the steps of: a) subjecting a compound of formula (II) to an enzymatic diastereomeric resolution in the presence of a suitable amount of enzyme chosen from Pig Liver Esterase or Porcine Pancreatic Lipase b) recovering said compounds of formula (I) and (VII). The invention also provides a process for producing compounds of formula (III) and (X); said process comprising the steps of: a) subjecting a compound of formula (IV) to an enzymatic diastereomeric resolution in the presence of a suitable amount of enzyme chosen from *Candida Antarctica* "A" lipase, *Candida Antarctica* "B" lipase, *Candida Lypolitica* Lipase or *Rhizomucor Miehei* Lipase b) recovering said compound of formula (III) and (X).

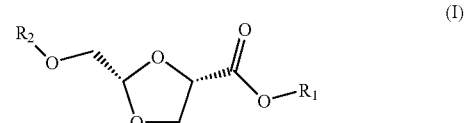

(I)

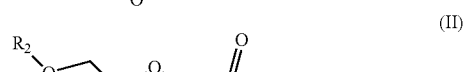

(II)

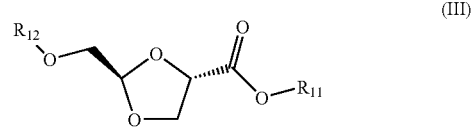

(III)

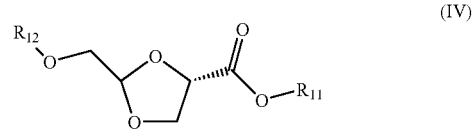

(IV)

28 Claims, No Drawings

STEREOSELECTIVE PROCESS FOR THE PRODUCTION OF DIOXOLANE NUCLEOSIDE ANALOGUES

This application is the U.S. National Phase under 35 U.S.C. §371 of International Application PCT/CA2003/001798, filed Nov. 18, 2003, which claims the benefit of U.S. Provisional Application No. 60/426,821, filed Nov. 18, 2002.

This application claims the benefit of U.S. Provisional Application No. 60/426,821, filed Nov. 18, 2002.

FIELD OF THE INVENTION

The present invention relates to a stereoselective process for the production of dioxolane nucleoside analogues and their intermediates.

BACKGROUND OF THE INVENTION

Nucleoside analogues are an important class of therapeutic agents. More particularly, dioxolane nucleoside analogues in which a substituted 1,3-dioxolane is replacing the carbohydrate found in natural nucleoside have shown to have biological activity.

Dioxolane analogues were first reported by Belleau et al. in EP 0337713 published Oct. 19, 1989, in U.S. Pat. No. 5,041,449 issued Aug. 20, 1991 and U.S. Pat. No. 5,270,315 issued Dec. 14, 1993.

9-(β-D-2-hydroxymethyl-1,3-dioxolane-4-yl)-2,6-diaminopurine (β-D-DAPD) and 9-(β-D-hydroxymethyl 1,3-dioxolane-4-yl)-9-guanine (β-D-DXG) have been reported by Gu et al. (*Antimicrob. Agents Chemother.* (1999), 43(10), pp 2376-2382 and *Nucleosides Nucleotides* (1999), 18(4&5), pp 891-892) to have useful efficacy against HIV-1 in various cell system.

Additionally, it was also reported (Weitman et al *Clinical Cancer Research* (2000), 6(4), pp 1574-1578 and Giles et al *Journal of Clinical Oncology* (2001), 19(3), pp 762-771 and also Gourdeau et al *Cancer Chemother. Pharmacol.* (2001), 47(3), pp 236-240) that 1-(β-L-2-hydroxymethyl-1,3-dioxolane-4-yl)-cytosine (β-L-OddC, troxacitabine) have shown efficacy for the treatment of various forms of cancers (e.g. solid tumours, adult leukemia and lymphomas).

Dioxolane intermediates such as 2-Benzoyloxymethyl-[1,3]dioxolane-4-carboxylate esters are important intermediates used in the synthesis of dioxolane nucleoside analogues as described in PCT publication number WO 97/21706 by MANSOUR, Tarek et al. 19 Jun. 1997, PCT publications number WO 00/47759 by CIMPOIA, Alex et al. 17 Aug. 2000, and PCT publication number WO 00/39143 by NGUYEN-BA, Nghe et al. 6 Jul. 2000. For the past years, literature has reported efforts directed toward development of bio-resolution methods. Enzymatic resolutions have the advantages of using catalytic amount of enzymes, being economical and reusable, and being environment friendly. Therefore, the identification of suitable enzymes for carrying diastereomeric resolution of 2-benzoyloxymethyl-[1,3]dioxolane-4-carboxylate esters is highly desirable.

SUMMARY OF THE INVENTION

In one aspect, the present invention provides a process for producing a compound of formula I:

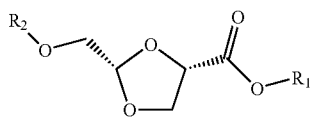

said process comprising the steps of:
a) subjecting a compounds of formula II:

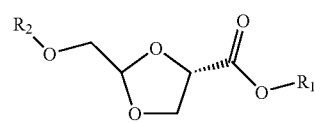

to an enzymatic diastereomeric resolution in the presence of a suitable amount of enzyme chosen from Pig Liver Esterase or Porcine Pancreatic Lipase;
b) recovering said compound of formula I
wherein;
$R_1$ is chosen from $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl; and
$R_2$ is a hydroxyl protecting group.

In another aspect, there is provided a process for producing a compound of formula III:

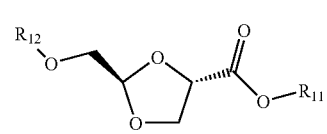

said process comprising the steps of:
a) subjecting a compounds of formula IV:

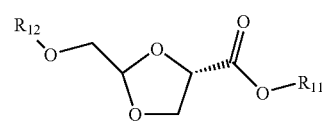

to an enzymatic diastereomeric resolution in the presence of a suitable amount of enzyme chosen from *Candida Antarctica* "A" lipase, *Candida Antarctica* "B" lipase, *Candida Lypolitica* Lipase or *Rhizomucor Miehei* Lipase;
b) recovering said compound of formula III;
wherein;
$R_{11}$ is chosen from $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl; and
$R_{12}$ is a hydroxyl protecting group.

DETAILED DESCRIPTION OF THE INVENTION

The present invention generally relates to an enzymatic diastereomeric resolution process for the production of dioxolane nucleoside analogues and their intermediates.

In one embodiment, the process of the present invention comprises those wherein the following embodiments are present, either independently or in combination.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents a straight chain, branched chain or cyclic hydrocarbon moiety which may optionally be substituted by one or more of: halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl; or Rc and Rd are taken together with the oxygens to form a 5 to 10 membered heterocycle;

or $R_{13}$ and $R_{14}$ are taken together with the nitrogen to form a 3 to 10 membered heterocycle. Useful examples of alkyls include isopropyl, ethyl, fluorohexyl or cyclopropyl. The term alkyl is also meant to include alkyls in which one or more hydrogen atoms is replaced by an oxygen, (e.g. a benzoyl) or an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "alkoxy" represents an alkyl which is covalently bonded to the adjacent atom through an oxygen atom.

The term "aryl" represents a carbocyclic moiety containing at least one benzenoid-type ring which may optionally be substituted by one or more of halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl; or Rc and Rd are taken together with the oxygens to form a 5 to 10 membered heterocycle;

or $R_{13}$ and $R_{14}$ are taken together with the nitrogen to form a 3 to 10 membered heterocycle. Examples of aryl include phenyl and naphthyl.

The term "arylalkyl" represents an aryl group attached to the adjacent atom by a $C_{1-6}$ alkyl (e.g., benzyl).

The term "aryloxy" represents an aryl which is covalently bonded to the adjacent atom through an oxygen atom.

The term "Acyl" is defined as a radical derived from a carboxylic acid, obtained by replacement of the —OH group. Like the acid to which it is related, an acyl radical may be straight chain, branched chain or cyclic aliphatic or aromatic, optionally substituted by one or more of halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;
or Rc and Rd are taken together with the oxygens to form a 5 to 10 membered heterocycle;

or $R_{13}$ and $R_{14}$ are taken together with the nitrogen to form a 3 to 10 membered heterocycle. Useful examples of acyl includes acetyl, propionyl, pivaloyl, hexanoyl, trifluoroacetyl, cyclohexanoyl and benzoyl.

"Acyloxy" is defined as an acyl group attached to the adjacent group by an oxygen atom (e.g. acetoxy, benzoyloxy).

As used in this application, the term "cycloalkyl" represents an "alkyl" as defined above which forms a ring (e.g. Cyclopropyl, cyclopentyl or cyclohexyl)

The term "cycloalkylamino" represents a cycloalkyl which is covalently bonded to the adjacent atom through a nitrogen atom.

The term "alkanol" represents an "alkyl" moiety for which one of the hydrogen has been replaced by an hydroxyl group (e.g. isopropanol, ethanol, or cyclopropanol). The term alkanol is also meant to include alkanol in which one or more hydrogen atoms is replaced by an halogen, more preferably, the halogen is fluoro (e.g. $CF_3CH_2OH$).

The term "independently" means that a substituent can be the same or different definition for each item.

The term "hydroxyl protecting group" is well known in the field of organic chemistry. Such protecting groups may be found in T. Greene, *Protective Groups In Organic Synthesis*, (John Wiley & Sons, 1981). Example of hydroxy protecting groups include but are not limited to benzyl, acetyl, benzoyl, pivaloyl and isopropyloxycarbonyl.

A "dioxolane ring" is any substituted or unsubstituted five member monocyclic ring that has an oxygen in the 1 and 3 positions of the ring as illustrated below:

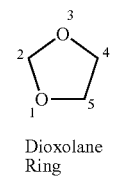

Dioxolane Ring

Halogens are chosen from F, Cl, I, and Br.

As used in this application, the term "purine or pyrimidine base or an analogue" is meant to be a purine or pyrimidine base found in a nucleotide or an analogue thereof which mimics such bases in that their structures (the kinds of atoms and their arrangement) are similar to the normal bases but may possess additional or lack certain of the functional properties of the normal bases. Such analogues include those derived by replacement of a CH moiety by a nitrogen atom (for example, 5-azapyrimidines such as 5-azacytosine) or vice versa (for example 7-deazapurines, such as 7-deazaadenosine or 7-deazaguanosine) or both (e.g. 7-deaza, 8-azapurines). Analogues of such bases also include those compounds wherein ring substituents are either incorporated, removed or modified by conventional substituents known in the art e.g. halogen, hydroxyl, amino, $C_{1-6}$ alkyl. Such purine or pyrimidine bases, analogues and derivatives will be well known to those skilled in the art.

The compounds described herein also include pharmaceutically acceptable salts of said compounds.

The term "pharmaceutically acceptable salts" of the compounds is meant to include those compounds derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4+$ (where R is $C_{1-4}$ alkyl) salts.

As used in this application, the term "suitable amount of enzyme" that can be used in the present invention is not particularly limited. It will be appreciated by a person of skill in the art that the amount of enzyme used will be selected in order to obtain a sufficient chemical transformation of the starting material, to obtain the desired purity or the desired yield of the reaction product, the desired reaction time or a combination of those. A useful example of "suitable amount of enzyme" may be in a weight ratio of between about 1% and 200% of enzyme with respect to the compounds of formula II or IV.

It will be appreciated by those skilled in the art that the enzymatic diastereomeric resolution may be carried out in a variety of solvent. Such solvents useful to carry out the desired process should not adversely affect the reaction. Useful examples of solvents include: water, $C_{1-12}$ alkanol (e.g. ethanol, butanol, t-amyl alcohol and 3-methyl-3-pentanol), toluene, acetonitrile, tetrahydrofuran, dimethylformamide, dimethylsulfonamide, N-methylpyrrolidone, isooctane, t-butylmethyl ether, and mixtures. The mixtures of solvent may be monophasic (e.g. water and isopropanol mixture) or biphasic and optionally use phase transfer catalysts well known in the art.

Aqueous solvent may be buffered if desired. Useful examples of buffer include: formate, acetate, phosphate, TRIS, citrate and borate. It will be readily apparent to a person of ordinary skill how such buffer or a different buffer may be prepared. Alternatively, premixed buffers in a range of pH values may be purchased from commercial laboratory supply. The use of a pH meter (or other pH measuring tool) to measure pH of the buffered solution is also possible.

The pH range suitable for use in this invention will be readily determined by a person of ordinary skill in the field. The selected pH will allow the process to occur under the reaction conditions, and provide the desired product without adversely affecting the reaction or extensively deactivating the enzyme.

In further embodiments of the invention:
the process is carried out in the pH range of about 4 to 9;
the process is carried out in the pH range of about 6 to 8;
the process is carried out in the pH range of about 6.8 to 7.2.

The concentration range of enzyme that can be used in the present invention is not particularly limited. For example the concentration of enzyme with respect to the solvent or solution may be from about 1 mg/ml to about 200 mg/ml. Alternatively, the concentration of enzyme with respect to the solvent or solution may be:
from about 1 mg/ml to about 100 mg/ml;
from about 5 mg/ml to about 20 mg/ml;
about 10 mg/ml;
about 7.5 mg/ml.

It will also be appreciated that the enzymes useful to carry out the desired process may be the cell free extract obtained after removal of cell debris used as the source of the enzyme or crude enzyme may be isolated by standard methods (e.g. fractional precipitation) and the resultant powder used as the enzyme. Alternatively, immobilized, purified, soluble or engineered enzyme may be used. Example of such enzyme technology may be found in "Enzyme Catalysis in Organic Synthesis: A Comprehensive Handbook", 2nd Edition; by Karlheinz Drauz and Herbert Waldmann (Wiley publisher).

In one embodiment, the process of the present invention is further comprising the step of recovering the enzyme used in the enzymatic diastereomeric resolution.

The temperature suitable for the use of this invention will be readily determined by a person of ordinary skill in the field. The selected temperature will allow the process to occur under the reaction conditions, and provide the desired product without adversely affecting the reaction or extensively deactivating the enzyme.

In further embodiments of the invention:
the process is carried out at a temperature in the range of about 5 to 50° C.;
the process is carried out at a temperature in the range of about 20 to 40° C.;
the process is carried out at about room temperature;
the process is carried out at a temperature of about 30° C.

The concentration range of compounds II or IV in the process may be as low as 0.1% or as high as 100%, or more if desired. Alternatively, the concentration is in the range of from about 1% to about 50%. or the concentration is in the range of from about 5% to about 15%. Alternatively, the concentration is about 12.5% or about 11.2%. The concentration is expressed in percent (%) and represent the amount in grams of compound per unit volume of solvent or solution (e.g. 50 g of compound/400 ml aqueous Phosphate buffer X 100=12.5%). The enzymatic diastereomeric resolution may be carried out on a solution, an emulsion or a suspention of compound II as well.

In one embodiment, the present invention provides a process for producing a compound of formula I:

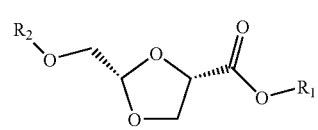

said process comprising the steps of:
a) subjecting a compounds of formula II:

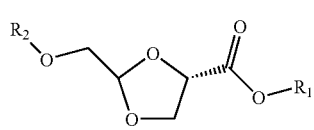

to an enzymatic diastereomeric resolution in the presence of a suitable amount of enzyme chosen from Pig Liver Esterase or Porcine Pancreatic Lipase;
b) recovering said compound of formula I
wherein each of $R_1$ and $R_2$ are as defined above.

It will be appreciated by those skilled in the art that compound of formula II, may be represented as well by formula IIa and IIb. Such mixture of compounds of formula IIa and IIb may be present in various ratios such as from about 1% to about 99% of IIa vs IIb (e.g. 1 to 1 or 1.5 to 1 or 2 to 1). All such possible ratios are included within the scope of the invention.

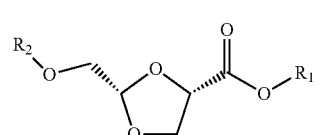

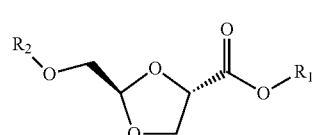

In further embodiments:
R$_1$ is C$_{1-12}$ alkyl;
R$_1$ is C$_{1-6}$ alkyl;
R$_1$ is methyl.

In further embodiments:
R$_2$ is chosen from: CO—C$_{1-6}$ alkyl, CO—C$_{6-12}$ aryl, CO—C$_{1-6}$ alkoxy, CO—C$_{6-12}$ aryloxy, or CO—C$_{6-12}$ aralkyl;
R$_2$ is CO—C$_{6-12}$ aryl;
R$_2$ is benzoyl.

In one embodiment, the enzyme is Pig Liver Esterase.
In another embodiment, the enzyme is Porcine Pancreatic Lipase.
In one embodiment, the suitable amount of enzyme is used in a weight ratio of about 0.1% to about 100% with respect to the compound of formula II.
In one embodiment, the suitable amount of enzyme is used in a weight ratio of about 1% to about 25% with respect to the compound of formula II.
In a further embodiment, the suitable amount of enzyme is used in a weight ratio of about 5% to about 10% with respect to the compound of formula II.

In further embodiments:
the compound of formula I has a diastereomeric purity of at least 80%;
the compound of formula I has a diastereomeric purity of at least 90%;
the compound of formula I has a diastereomeric purity of at least 95%;
the compound of formula I has a diastereomeric purity of at least 98%.

In one embodiment, the present invention provides a process for producing a compound of formula I:

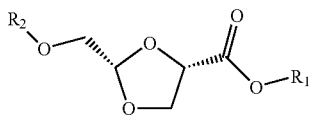

I said process comprising the steps of:
a) subjecting a compounds of formula II:

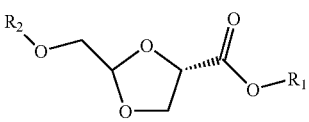

II to an enzymatic diastereomeric resolution in the presence of a suitable amount of enzyme chosen from Pig Liver Esterase or Porcine Pancreatic Lipase;
b) recovering said compound of formula I;
and further comprising the steps of:
c) replacing the functional group at position C4 of the compound of formula I to produce a compound of formula V:

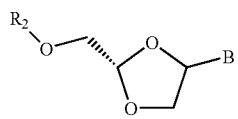

V d) removing the group R$_2$ of said compound of formula V;
e) recovering a compound of formula VI:

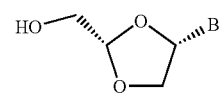

VI or a pharmaceutically acceptable salt thereof; wherein;
B is purine or pyrimidine base or an analogue thereof; and wherein each of R$_1$ and R$_2$ are as defined above.

In one embodiment, B is chosen from:

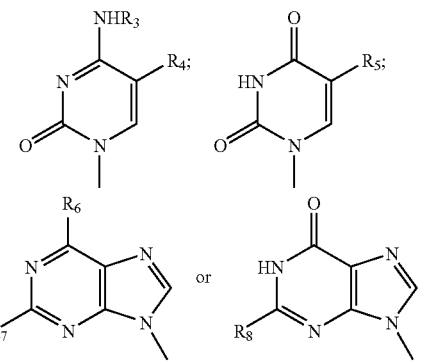

wherein;
R$_3$ is chosen from H, C$_{1-6}$ alkyl, C$_{1-6}$ acyl and CO—R$_9$; wherein R$_9$ is H or C$_{1-6}$ alkyl;
R$_4$ and R$_5$ are each independently chosen from H, C$_{1-6}$ alkyl, bromide, chloride, fluoride, iodide or CF$_3$; and R$_6$, R$_7$ and R$_8$ are each independently chosen from H, bromide, chloride, fluoride, iodide, amino, hydroxyl or C$_{3-6}$ cycloalkylamino.

In another embodiment, B is chosen from:

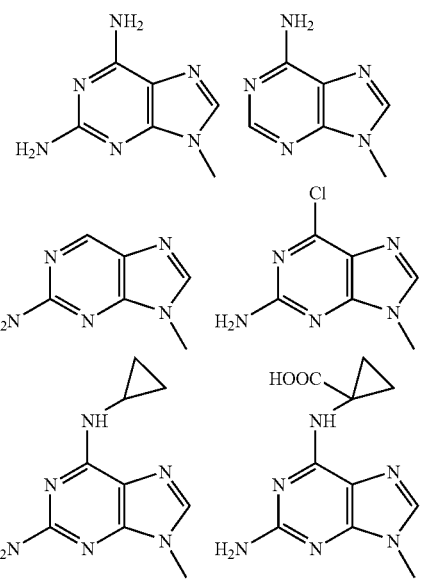

-continued

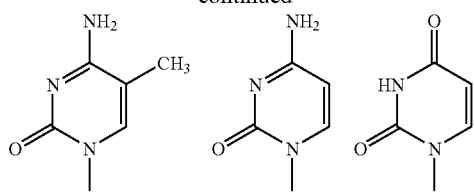

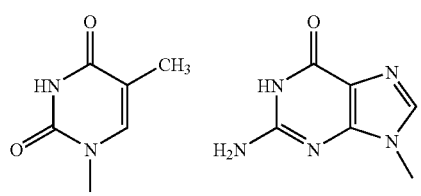

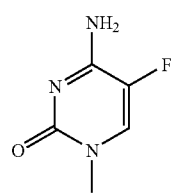

In one embodiment, the present invention provides a process for producing a compound of formula I:

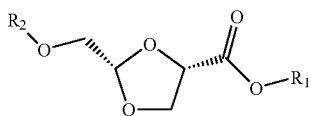

said process comprising the steps of:
  a) subjecting a compounds of formula II:

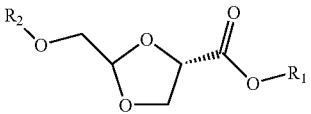

to an enzymatic diastereomeric resolution in the presence of a suitable amount of enzyme chosen from Pig Liver Esterase or Porcine Pancreatic Lipase;
  b) recovering said compound of formula I;
and further comprising the step of recovering a compound of formula VII:

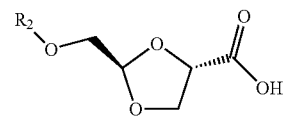

wherein each of $R_1$ and $R_2$ is as defined above.

In one embodiment, the present invention provides a process for producing a compound of formula III:

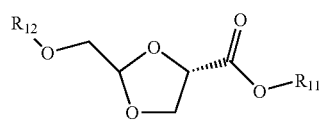

said process comprising the steps of:
  a) subjecting a compounds of formula IV:

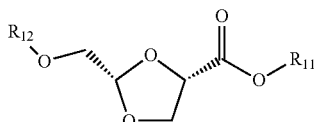

to an enzymatic diastereomeric resolution in the presence of a suitable amount of enzyme chosen from *Candida Antarctica* "A" lipase, *Candida Antarctica* "B" lipase, *Candida Lypolitica* Lipase or *Rhizomucor Miehei* Lipase;
  a) recovering said compound of formula III;
  wherein $R_{11}$ and $R_{12}$ are as described above.

It will be appreciated by those skilled in the art that compound of formula IV, may be represented as well by formula IVa and IVb. Such mixture of compounds of formula IVa and IVb may be present in various ratios such as from about 1% to about 99% of IVa vs IVb (e.g. 1 to 1 or 1.5 to 1 or 2 to 1). All such possible ratios are included within the scope of the invention.

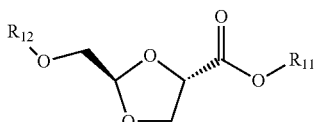

In further embodiments:
  $R_{11}$ is $C_{1-12}$ alkyl;
  $R_{11}$ is $C_{1-6}$ alkyl;
  $R_{11}$ is methyl.
In further embodiments:
  $R_{12}$ is chosen from: CO—$C_{1-6}$ alkyl, CO—$C_{6-12}$ aryl, CO—$C_{1-6}$ alkoxy, CO—$C_{6-12}$ aryloxy, or CO—$C_{6-12}$ arylalkyl;
  $R_{12}$ is CO—$C_{6-12}$ aryl;
  $R_{12}$ is benzoyl.
In one embodiment, the enzyme is *Candida Antarctica* "A" lipase.
In a further embodiment, the enzyme is *Candida Antarctica* "B" lipase.
In still a further embodiment, the enzyme is *Candida Lypolitica* Lipase.
In still a further embodiment, the enzyme is *Rhizomucor Miehei* Lipase.
In one embodiment, the suitable amount of enzyme is used in a weight ratio of about 0.1% to about 100% with respect to the compound of formula IV.

In one embodiment, the suitable amount of enzyme is used in a weight ratio of about 1% to about 25% with respect to the compound of formula IV.

In one embodiment, the suitable amount of enzyme is used in a weight ratio of about 5% to about 10% with respect to the compound of formula IV.

In further embodiments:
the compound of formula III has a diastereomeric purity of at least 80%;
the compound of formula III has a diastereomeric purity of at least 90%;
the compound of formula III has a diastereomeric purity of at least 95%;
the compound of formula III has a diastereomeric purity of at least 98%.

In one embodiment, the present invention provides a process for producing a compound of formula III:

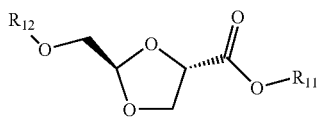
III said process comprising the steps of:
a) subjecting a compounds of formula IV:

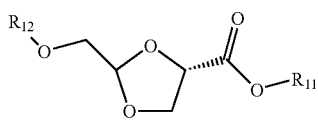
IV to an enzymatic diastereomeric resolution in the presence of a suitable amount of enzyme chosen from *Candida Antarctica* "A" lipase, *Candida Antarctica* "B" lipase, *Candida Lypolitica* Lipase or *Rhizomucor Miehei* Lipase;
b) recovering said compound of formula III;
and further comprising the steps of:
c) replacing the functional group at position C4 of the compound of formula III to produce a compound of formula VIII:

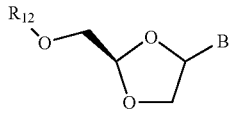
VIII d) removing the group $R_{12}$ of said compound of formula VIII;
e) recovering a compound of formula IX:

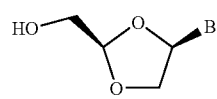
IX or a pharmaceutically acceptable salt thereof; wherein;
B is purine or pyrimidine base or an analogue thereof; and
Each of $R_{11}$ and $R_{12}$ are as defined above.

In one embodiment, B is chosen from:

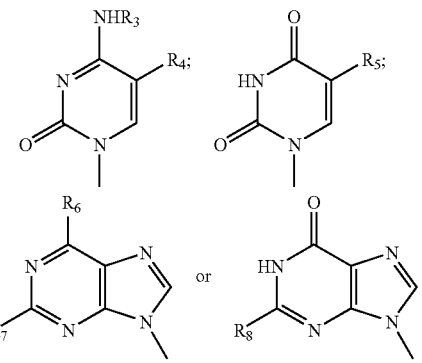

wherein;
$R_3$ is chosen from H, $C_{1-6}$ alkyl, $C_{1-6}$ acyl and CO—$R_9$; wherein $R_9$ is H or $C_{1-6}$ alkyl;
$R_4$ and $R_5$ are each independently chosen from H, $C_{1-6}$ alkyl, bromide, chloride, fluoride, iodide or $CF_3$; and $R_6$, $R_7$ and $R_8$ are each independently chosen from H, bromide, chloride, fluoride, iodide, amino, hydroxyl or $C_{3-6}$ cycloalkylamino.

In another embodiment, B is chosen from:

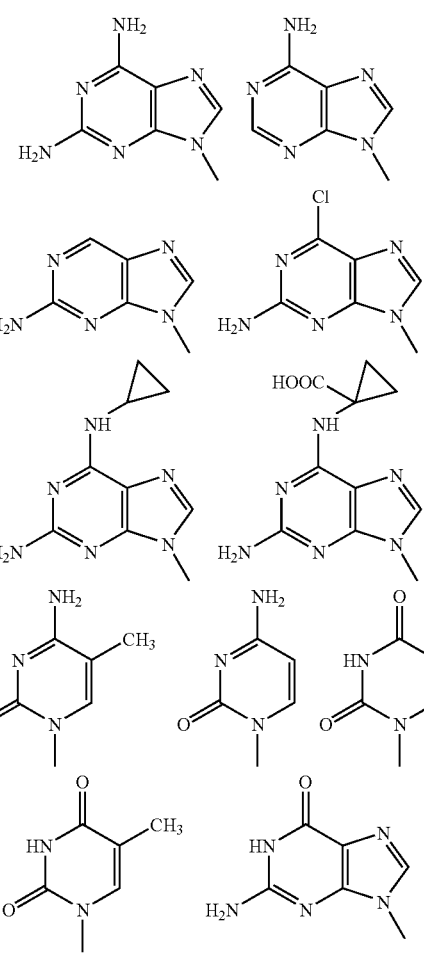

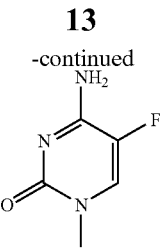

In one embodiment, the present invention provides a process for producing a compound of formula III:

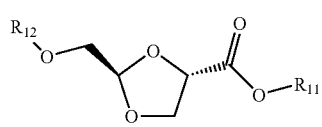

said process comprising the steps of:
a) subjecting a compounds of formula IV:

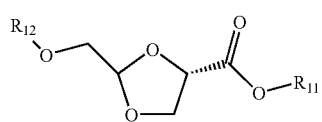

to an enzymatic diastereomeric resolution in the presence of a suitable amount of enzyme chosen from *Candida Antarctica* "A" lipase, *Candida Antarctica* "B" lipase, *Candida Lypolitica* Lipase or *Rhizomucor Miehei* Lipase;
b) recovering said compound of formula III;
and further comprising the step of recovering a compound of formula X:

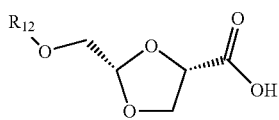

wherein $R_{11}$ and $R_{12}$ are as described above.

It will also be appreciated by a skilled technician that a round bottomed flask or a standard laboratory reactor, fitted with an overhead stirrer or a magnetic stirring bar, may be used to give more complete mixing of the system without undue shear. Initially, the compound II may form a separate phase at the bottom of the reactor and over the course of the reaction becomes more evenly dispersed.

It will be appreciated that agitation may be used if desired. The suitable rate of agitation that may be used during the steps of addition of the enzyme, during the addition of base (to prevent high local pH that may be unsuitable for the reagents) or continuously during the process will be selected in order to allow the process to occur under the reaction conditions, and provide the desired product without adversely affecting the reaction or extensively deactivating the enzyme.

A person of ordinary skill in the art will appreciate that the dioxolane compound used to carry the enzymatic diastereomeric resolution (scheme 1 and 2) may be prepared using known procedures. Examples of such procedure are described in:

1. PCT publication number WO 97/21706 by MANSOUR, Tarek et al. 19 Jun. 1997;
2. PCT publications number WO 00/47759 by CIMPOIA, Alex et al. 17 Aug. 2000; and
3. PCT publication number WO 00/39143 by NGUYEN-BA, Nghe et al. 6 Jul. 2000.

In one embodiment, the processes of this invention may be carried out as illustrated in general scheme 1 or scheme 2.

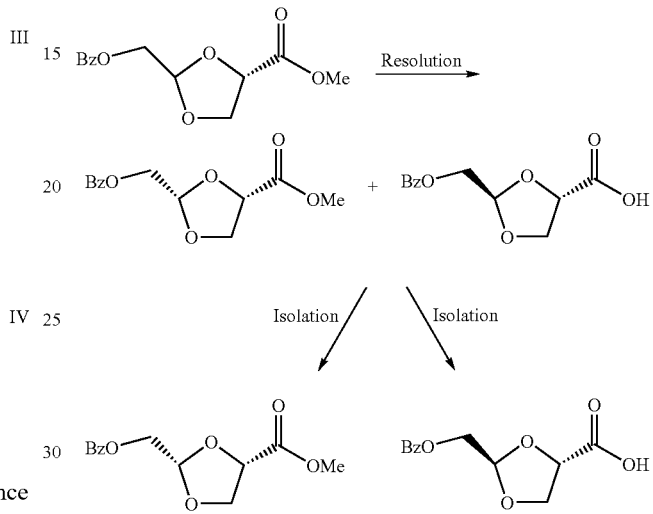

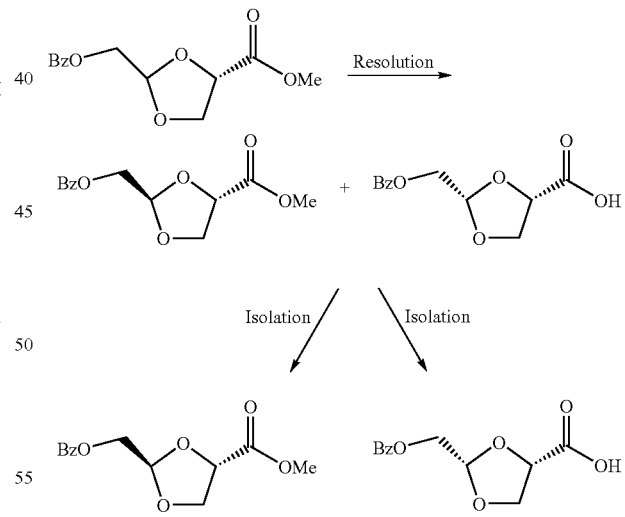

There are several examples known by skilled artisan on how to prepare dioxolane nucleoside analogues from dioxolane compounds of formula I or formula III. For example, methods of linking a purine, a pyrimidine base or an analogue at the C-4 position of a dioxolane ring are described in: PCT publication number WO 97/21706 and PCT publication number WO 00/39143. Scheme 3 and scheme 4 are illustrating methods of linking a purine, a pyrimidine base or an analogue to a dioxolane ring.

SCHEME 3

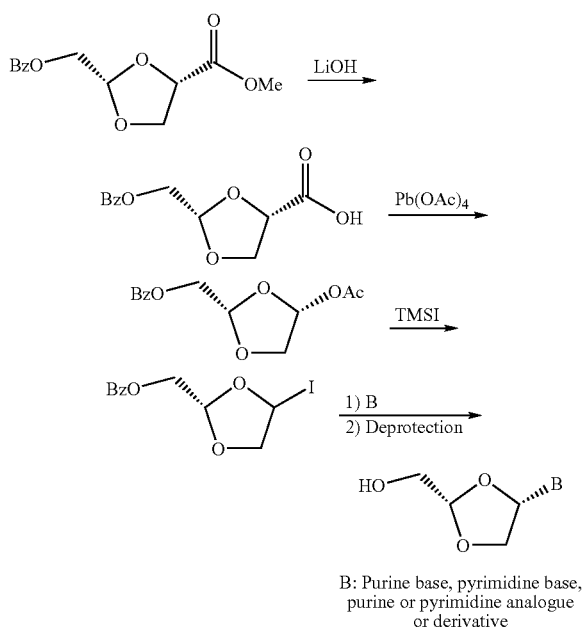

B: Purine base, pyrimidine base, purine or pyrimidine analogue or derivative

SCHEME 4

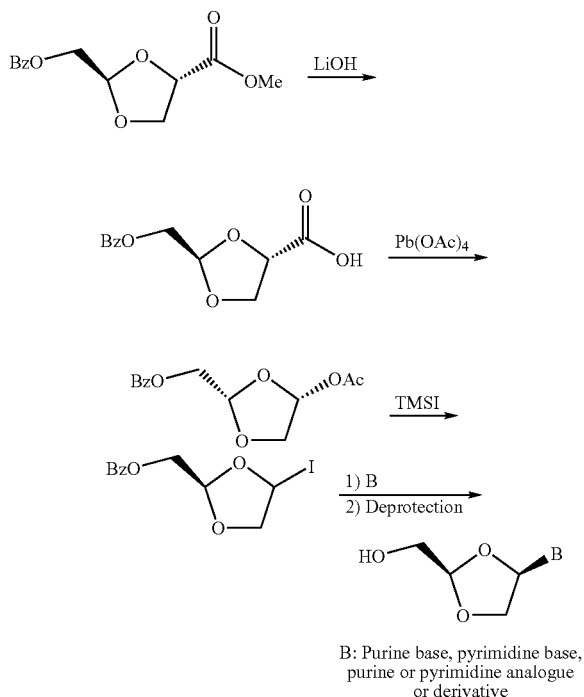

B: Purine base, pyrimidine base, purine or pyrimidine analogue or derivative

After hydrolysis of the methyl ester and oxidative decarboxylation, the resulting dioxolane can be coupled to a purine, a pyrimidine base or an analogue and further deprotected to provide the desired dioxolane nucleoside analogues.

The following examples are provided to illustrate various embodiments of the present invention and shall not be considered as limiting in scope.

EXAMPLES

Example 1

2(S)-Benzoyloxymethyl-[1,3]dioxolane-4(S)-carboxylic acid methyl ester

2-Benzoyloxymethyl-[1,3]dioxolane-4(S)-carboxylic acid methyl ester (50 g, 1:1 cis to trans ratio) and a magnetic stir bar were charged to a 1 liter Erlenmeyer flask. An aqueous Phosphate buffer (400 ml, 0.3 M, pH=7.1) was then charged into the flask. The reaction flask was heated to 30° C. using an external water bath.

The pH of reaction mixture was adjusted to 7 with 1 N NaOH and then 4 g of Porcine Pancreatic Lipase powder was added in one portion. The resulting suspension was stirred moderately and the pH was maintained between 6.8 and 7.2 by the periodic addition of 2 N NaOH via pipette. Approximately 35 ml of 2 N NaOH was added over the course of the reaction. The reaction was monitored by HPLC analysis using a chiral column (CHIRACEL®OD; 0.46×25 cm) to determine optical purity of the unreacted ester and reaction conversion. (Samples were withdrawn at 1, 2, 4, 6 and 8 hours.) After 5 hours the reaction progress had stopped, so an additional 1.5 g of Porcine Pancreatic Lipase was added. Once the ratio of cis-ester to trans-ester was >98:2 (an additional 2.5 hours), the reaction was terminated by the addition of 200 ml of ethyl acetate.

Diatomaceous earth (15 g) was added and the biphasic mixture stirred for 5 minutes. The mixture was then filtered with gentle suction and the filter cake washed with two 25 ml portions of ethyl acetate. The biphasic mixture was transferred into a separatory funnel and allowed to settle until the two phases were separated as much as possible. A lower clear aqueous phase (ca. 400 ml) was drained out and then extracted once with ethyl acetate (25 ml). The combined organic layers and emulsion phase were washed twice with 100 ml saturated sodium bicarbonate and dried by washing once with 75 ml of saturated brine (If necessary, the product may be further dried by passing it through a small amount of anhydrous sodium sulfate). The solvent was then evaporated under reduced pressure to give 2(S)-Benzoyloxymethyl-[1,3]dioxolane-4(S)-carboxylic acid methyl ester as pale yellow liquid (25.8 g). Analysis by HPLC showed less than 2% of 2(R)-Benzoyloxymethyl-[1,3]dioxolane-4(S)-carboxylic acid methyl ester.

Example 2

2(R)-Benzoyloxymethyl-[1,3]dioxolane-4(S)-carboxylic acid methyl

2-Benzoyloxymethyl-[1,3]dioxolane-4(S)-carboxylic acid methyl ester (1.12 g of 1:1.27 mixture of 2(S)-Benzoyloxymethyl-[1,3]dioxolane-4(S)-carboxylic acid methyl ester and 2(R)-Benzoyloxymethyl-[1,3]dioxolane-4(S)-carboxylic acid methyl ester), was added to a 25 ml beaker containing a stir bar and 10 ml of 0.04 M pH 7.2 phosphate buffer. To this was added 75 mg of *Rhizomucor Miehei* Lipase and the pH readjusted to 7.2 with 2 N NaOH. The suspension was stirred using a magnetic stirrer and the reaction was allowed to proceed at room temperature. The pH was readjusted periodically by the addition of 2 N NaOH. The conversion was monitored by removing 50μ aliquots and analyzing by HPLC (CHIRACEL®OD; 0.46×25 cm column). After 1 hour the extent of hydrolysis was 25%. After 9 hours the reaction was stopped by extraction with dichloromethane (10 ml). The organic phase was collected and the aqueous phase re-extracted with dichloromethane (10 ml). A persistent emulsion formed, so diatomaceous earth was added (3 g) and the mixture filtered through a sintered glass funnel and the filter cake washed with dichloromethane (10 ml). The filtrate was separated and the combined organic phases extracted with saturated sodium bicarbonate (2×20 ml) and one portion of 5% brine (15 ml). The solution was dried over sodium sulfate and the solvent removed under reduced pressure. 2(R)-Benzoyloxymethyl-[1,3]dioxolane-4(S)-carboxylic acid methyl as a yellow oil (0.45 g) was obtained that contained approximately 3.5% of 2(S)-Benzoyloxymethyl-[1,3]dioxolane-4(S)-carboxylic acid methyl ester.

The enzymes useful to carry the process of the present invention can be obtained from Altus Biologics Inc. Cambridge, Mass.

The invention claimed is:

1. A process for producing a compound of formula I and a compound of formula VII:

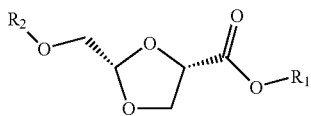

I

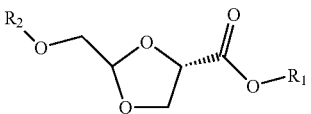

VII wherein
R$_1$ is C$_{1-12}$ alkyl, C$_{2-12}$ alkenyl, C$_{2-12}$ alkynyl, C$_{6-12}$ aryl, C$_{3-10}$ heterocycle, C$_{6-12}$ aralkyl or C$_{3-10}$ heteroaralkyl, and
R$_2$ is CO—C$_{1-6}$ alkyl, CO—C$_{6-12}$ aryl, CO—C$_{1-6}$ alkoxy, CO—C$_{6-12}$ aryloxy, or CO—C$_{6-12}$ arylalkyl;
said process comprising:
a) subjecting a compound of formula II:

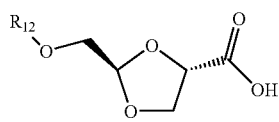

II to an enzymatic diastereomeric resolution in the presence of a suitable amount of Pig Liver Esterase enzyme or Porcine Pancreatic Lipase enzyme, wherein said resolution is conducted in the presence of a solvent selected from water, C$_{1-12}$ alkanol, toluene, acetonitrile, tetrahydrofuran, dimethylformamide, dimethylsulfonamide, N-methylpyrrolidone, isooctane, t-butylmethyl ether, and mixtures thereof; and
b) recovering compounds of formula I and formula VII.

2. The process according to claim 1, wherein R$_1$ is C$_{1-12}$ alkyl.

3. The process according to claim 1 wherein R$_2$ is CO—C$_{1-6}$ alkyl.

4. The process according to claim 1, wherein R$_2$ is CO—C$_{6-12}$ aryl.

5. The process according to claim 1, wherein the enzyme is Pig Liver Esterase.

6. The process according to claim 1, wherein the enzyme is Porcine Pancreatic Lipase.

7. The process according to claim 1, further comprising:
a) replacing the functional group at position C4 of the compound of formula I with B to produce a compound of formula V:

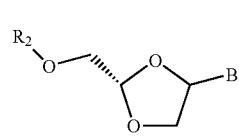

V wherein B is purine or pyrimidine base;
b) removing the group R$_2$ of said compound of formula V; and
c) recovering a compound of formula VI:

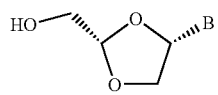

VI or a pharmaceutically acceptable salt thereof.

8. The process according to claim 7, wherein B is:

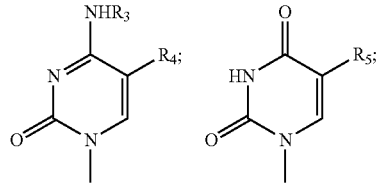

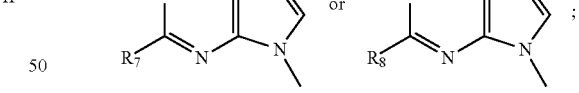

R$_3$ is H, C$_{1-6}$ alkyl, C$_{1-6}$ acyl, or CO—R$_9$;
R$_9$ is H or C$_{1-6}$ alkyl;
R$_4$ and R$_5$ are each independently H, C$_{1-6}$ alkyl, bromide, chloride, fluoride, iodide or CF$_3$; and
R$_6$, R$_7$ and R$_8$ are each independently H, bromide, chloride, fluoride, iodide, amino, hydroxyl, or C$_{3-6}$ cycloalkylamino.

9. A process according to claim 1, wherein R$_1$ is C$_{1-12}$ alkyl and R$_2$ is CO—C$_{6-12}$ aryl.

10. A process according to claim 1, wherein R$_1$ is methyl and R$_2$ is benzoyl.

11. A process for producing a compound of formula III and a compound of formula X:

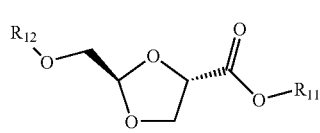

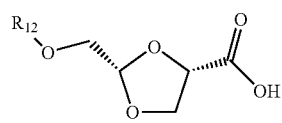

wherein
$R_{11}$ is $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl; and
$R_{12}$ is CO—$C_{1-6}$ alkyl, CO—$C_{6-12}$ aryl, CO—$C_{1-6}$ alkoxy, CO—$C_{6-12}$ aryloxy, or CO—$C_{6-12}$ arylalkyl,
said process comprising:
a) subjecting a compound of formula IV:

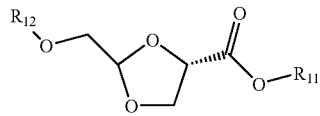

to an enzymatic diastereomeric resolution in the presence of a suitable amount of an enzyme, wherein said enzyme is *Candida Antarctica* "A" lipase, *Candida Antarctica* "B" lipase, *Candida Lypolitica* Lipase, or *Rhizomucor Miehei* Lipase, wherein said resolution is conducted in the presence of a solvent selected from water, $C_{1-12}$alkanol, toluene, acetonitrile, tetrahydrofuran, dimethylformamide, dimethylsulfonamide, N-methylpyrrolidone, isooctane, t-butylmethyl ether, and mixtures thereof; and
b) recovering compounds of formula III and formula X.

12. The process according to claim 11, wherein $R_{11}$ is $C_{1-12}$ alkyl.

13. The process according to claim 11, wherein $R_{12}$ is CO—$C_{1-6}$ alkyl.

14. The process according to claim 11, wherein $R_{12}$ is CO—$C_{6-12}$ aryl.

15. The process according to claim 11, wherein the enzyme is *Candida Antarctica* "A" lipase.

16. The process according to claim 11, wherein the enzyme is *Candida Antarctica* "B" lipase.

17. The process according to claim 11, wherein the enzyme is *Candida Lypolitica* Lipase.

18. The process according to claim 11, wherein the enzyme is *Rhizomucor Miehei* Lipase.

19. The process according to claim 11, further comprising:
a) replacing the functional group at position C4 of the compound of formula III with B to produce a compound of formula VIII:

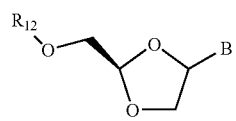

wherein B is purine or pyrimidine base;
b) removing group $R_{12}$ of said compound of formula VIII;
c) recovering a compound of formula IX:

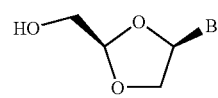

or a pharmaceutically acceptable salt thereof.

20. The process according to claim 19, wherein B is

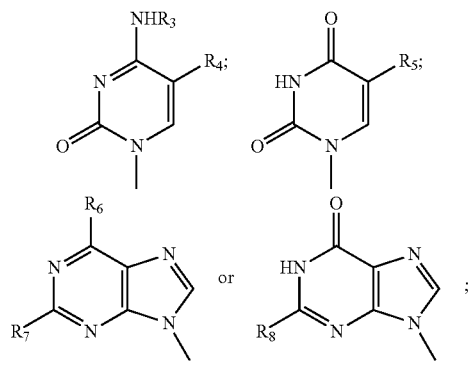

$R_3$ is H, $C_{1-6}$ alkyl, $C_{1-6}$ acyl and CO—$R_9$;
$R_9$ is H or $C_{1-6}$ alkyl;
$R_4$ and $R_5$ are each independently H, $C_{1-6}$ alkyl, bromide, chloride, fluoride, iodide or $CF_3$; and
$R_6$, $R_7$ and $R_8$ are each independently H, bromide, chloride, fluoride, iodide, amino, hydroxyl or $C_{3-6}$cycloalkylamino.

21. A process according to claim 11, wherein $R_{11}$ is $C_{1-12}$ alkyl and $R_{12}$ is CO—$C_{6-12}$ aryl.

22. A process according to claim 11, wherein $R_{11}$ is methyl and $R_{12}$ is benzoyl.

23. A process according to claim 1, wherein said process is carried out at a pH of 6 to 8, at a temperature in the range of 5 to 50° C., and the concentration of enzyme with respect to the solvent is 1 mg/ml to 100 mg/ml.

24. A process according to claim 11, wherein said process is carried out at a pH of 6 to 8, at a temperature in the range of 5 to 50° C., and the concentration of enzyme with respect to the solvent is 1 mg/ml to 100 mg/ml.

25. A process according to claim 1, wherein the weight ratio of the amount of enzyme to the amount of the compound of formula II is 1% to 25%.

26. A process according to claim 1, wherein the weight ratio of the amount of enzyme to the amount of the compound of formula II is 5% to 10%.

27. A process according to claim 11, wherein the weight ratio of the amount of enzyme to the amount of the compound of formula IV is 1% to 25%.

28. A process according to claim 11, wherein the weight ratio of the amount of enzyme to the amount of the compound of formula IV is 5% to 10%.

* * * * *